US011255030B2

(12) United States Patent
Pilz et al.

(10) Patent No.: US 11,255,030 B2
(45) Date of Patent: Feb. 22, 2022

(54) KNITTED FABRIC AND USE OF A KNITTED FABRIC

(71) Applicant: Pilz GmbH & Co. KG, Ostfildern (DE)

(72) Inventors: Thomas Pilz, Ostfildern (DE); Hansjürgen Horter, Ostfildern (DE); Karl Gönner, Ostfildern (DE); Oswald Rieder, Denkendorf (DE); Uwe Röder, Denkendorf (DE)

(73) Assignee: Pilz GmbH & Co. KG, Ostfildern (DE)

( * ) Notice: Subject to any disclaimer, the term of this patent is extended or adjusted under 35 U.S.C. 154(b) by 192 days.

(21) Appl. No.: 16/595,997

(22) Filed: Oct. 8, 2019

(65) Prior Publication Data

US 2020/0040492 A1    Feb. 6, 2020

Related U.S. Application Data

(63) Continuation of application No. PCT/EP2018/060367, filed on Apr. 23, 2018.

(30) Foreign Application Priority Data

Apr. 21, 2017   (DE) .......................... 102017108550.5

(51) Int. Cl.
*D04B 1/12*    (2006.01)
*G01V 3/08*    (2006.01)
(Continued)

(52) U.S. Cl.
CPC ............ *D04B 1/123* (2013.01); *A61B 5/6804* (2013.01); *D04B 1/14* (2013.01); *G01V 3/088* (2013.01); *D10B 2403/02431* (2013.01)

(58) Field of Classification Search
CPC .......... D04B 1/123; D04B 1/14; D04B 1/126; D04B 1/22; D04B 1/24; G01V 3/088;
(Continued)

(56) References Cited

U.S. PATENT DOCUMENTS

2005/0016220 A1* 1/2005 Okuno .................... D04B 7/26
66/64
2016/0018274 A1  1/2016 Seitz

FOREIGN PATENT DOCUMENTS

CN         1274270 A      11/2000
CN         1430765 A      7/2003
(Continued)

OTHER PUBLICATIONS

International Search report in corresponding International Application No. PCT/EP2018/060367, dated Jul. 24, 2018, with English translation.
(Continued)

*Primary Examiner* — Amy He
(74) *Attorney, Agent, or Firm* — Edell, Shapiro & Finnan, LLC

(57) ABSTRACT

A shaped knitted fabric (1*a*-1*f*) is provided comprising at least one first layer (10), into which a plurality of linear or flat, for example, strip-shaped, electroconductive structures (10*a*, 10*b*, 10*c*, 11*a*, 11*b*, 11*c*) made of an electroconductive yarn and linear or flat, for example strip-shaped, non-electroconductive structures (12) made of a non-electroconductive yarn are knitted such that the electroconductive structures (10*a*, 10*b*, 10*c*, 11*a*, 11*b*, 11*c*) are electrically insulated from one another, wherein each of the electroconductive structures (10*a*, 10*b*, 10*c*, 11*a*, 11*b*, 11*c*) can individually be electrically contacted and connected to an evaluation circuit (50).

17 Claims, 10 Drawing Sheets

(51) Int. Cl.
*D04B 1/14* (2006.01)
*A61B 5/00* (2006.01)

(58) Field of Classification Search
CPC ........... A61B 5/6804; A61B 5/00; A61B 5/05;
D10B 2403/02412; D10B 2403/02431
See application file for complete search history.

(56) References Cited

FOREIGN PATENT DOCUMENTS

| | | |
|---|---|---|
| CN | 1954399 A | 4/2007 |
| JP | 2009-42108 A | 2/2009 |
| JP | 2010-243240 A | 10/2010 |
| WO | 9964657 A | 12/1999 |
| WO | 9964657 A1 | 12/1999 |
| WO | 0175778 A1 | 10/2001 |
| WO | 2005091319 A1 | 9/2005 |
| WO | 2013120624 A1 | 8/2013 |

OTHER PUBLICATIONS

Office Action in corresponding Chinese Patent Application No. 201880026410.X dated Nov. 30, 2020, with English translation.
Office Action in corresponding Chinese Patent Application No. 201880026410.X dated Jun. 10, 2020, with English translation.

* cited by examiner

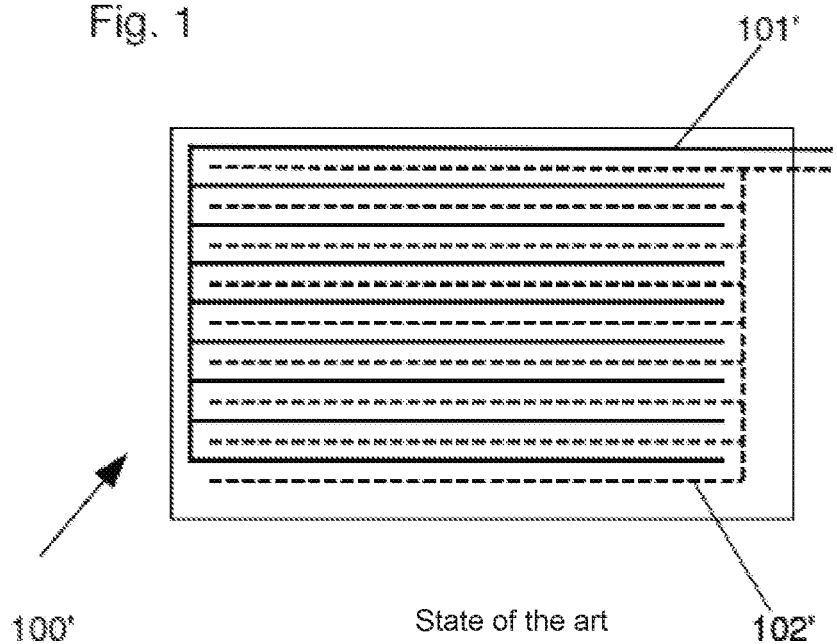
Fig. 1 State of the art
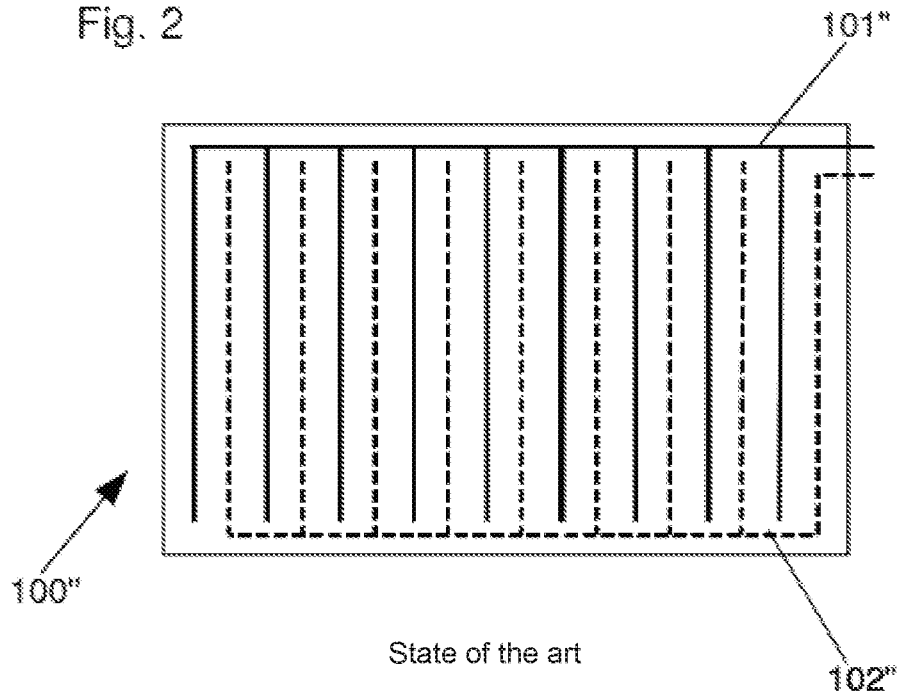
Fig. 2 State of the art

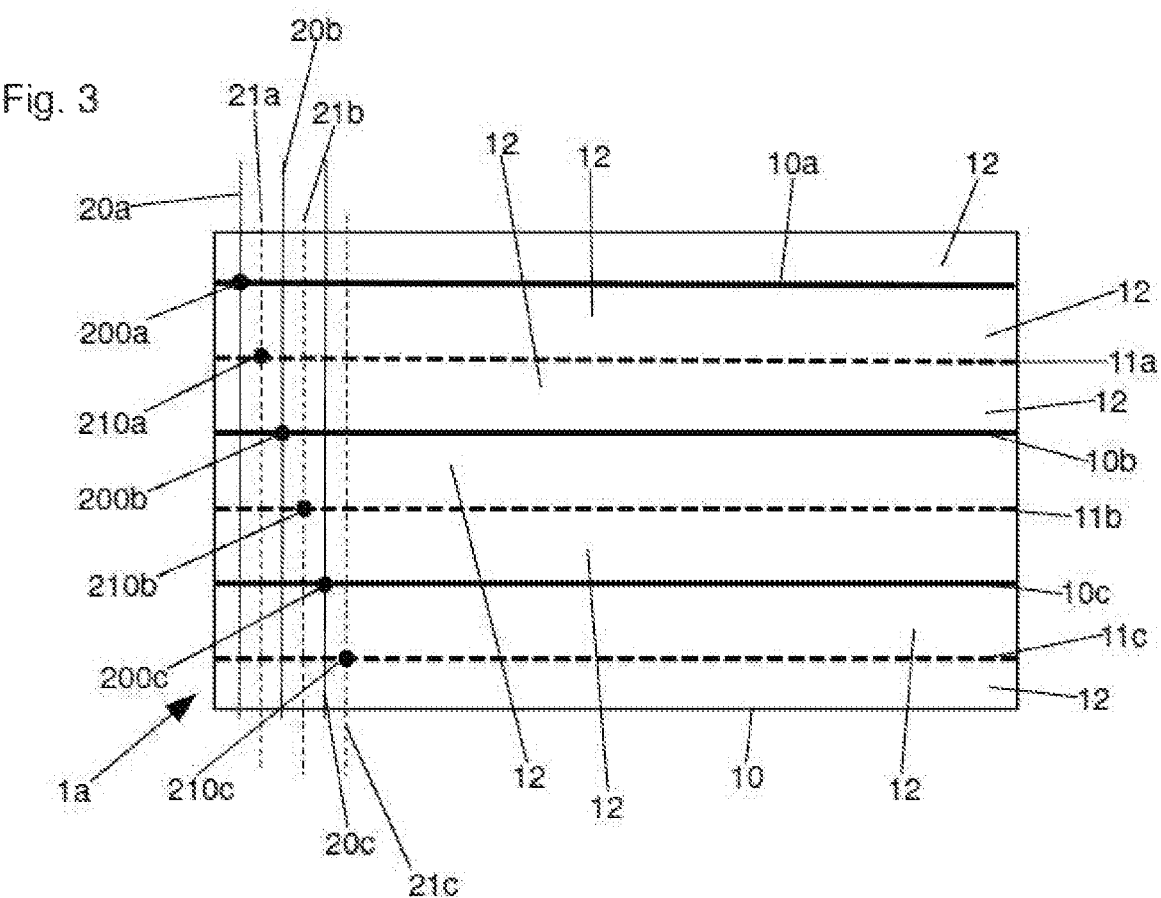

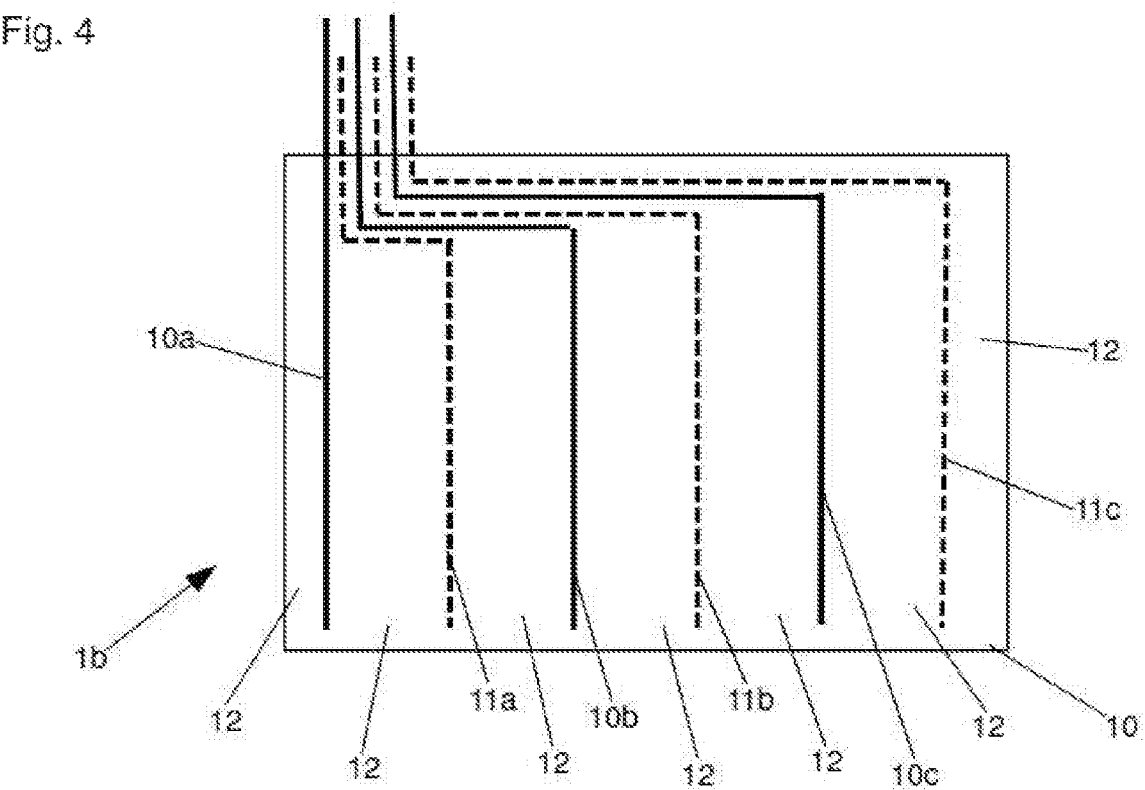

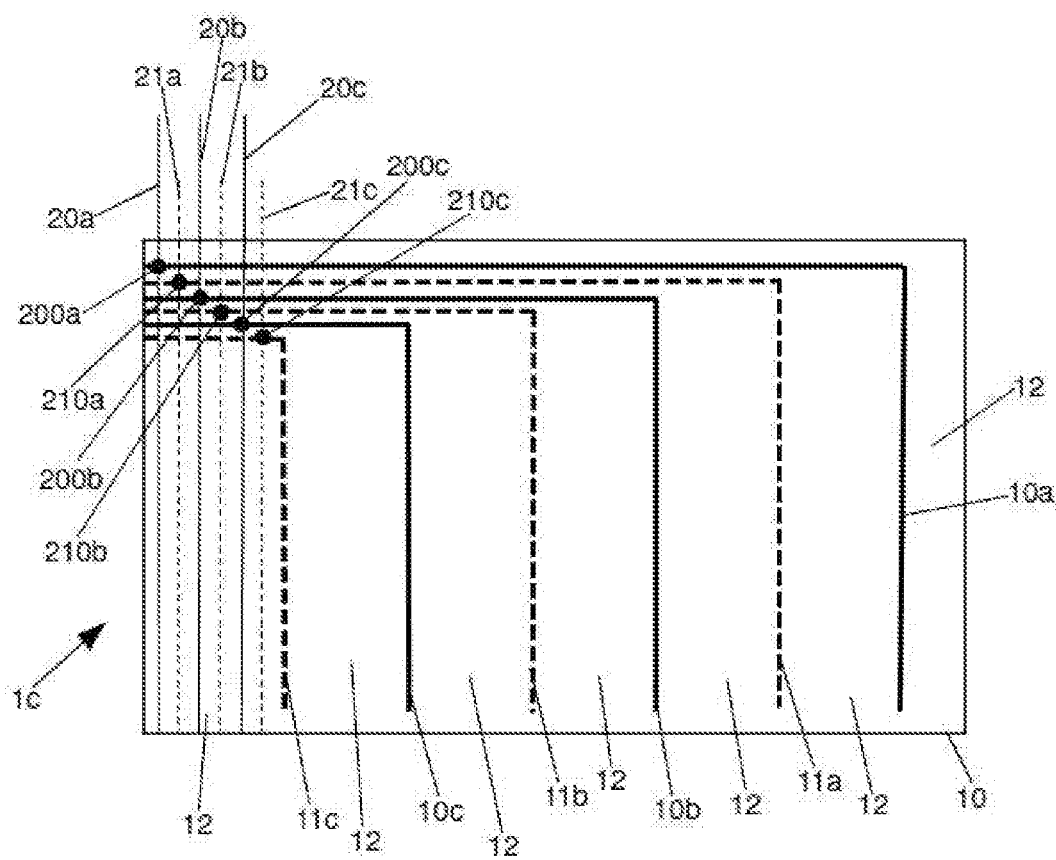

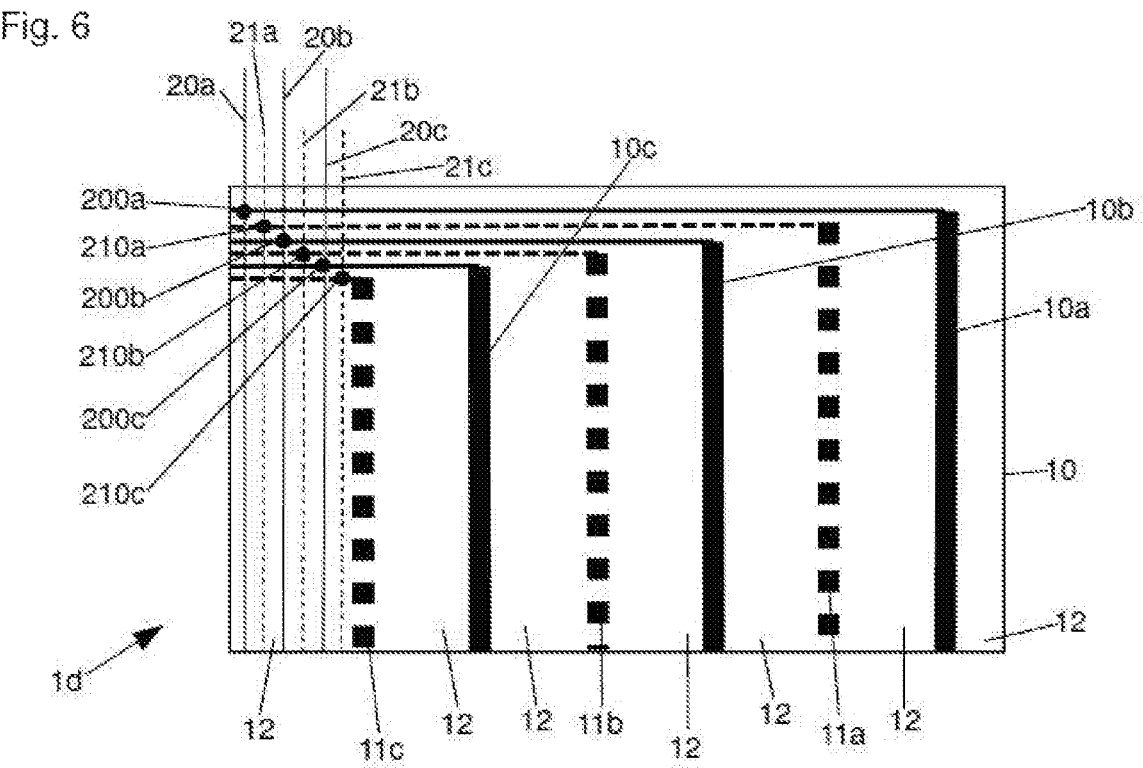

KNITTED FABRIC AND USE OF A KNITTED FABRIC

CROSS REFERENCE TO RELATED APPLICATIONS

This application is a continuation of International Application No. PCT/EP2018/060367, filed on Apr. 23, 2018, which claims priority under 35 U.S.C. § 119 to Application No. DE 102017108550.5 filed on Apr. 21, 2017, the entire contents of which are hereby incorporated by reference.

TECHNICAL FIELD

A shaped knitted fabric is provided, together with methods of using the fabric.

BACKGROUND

Definition

As used herein, the term "shaped knitted fabric" refers to knitted fabrics that comprise a two-dimensional or a three-dimensional structure and, at least in sections, are produced by knitting.

Electroconductive textile structures, in particular sensory or sensing fabrics, are known from the state of the art in a variety of forms. They can be used in a variety of technical applications, for example as sensors.

A sensing or sensory fabric having a fabric layer, in which the electroconductive threads of the fabric layer cross at specific crossing points, is known from U.S. Pat. No. 4,795,998 A. The contact resistance between the threads resting against one another at the crossing points changes as a function of an external force acting on the sensory fabric. It is thus possible to detect a force acting on the fabric at one of the crossing points of the electroconductive threads, by determining the change in the electrical contact resistance with the aid of a suitable evaluation circuit.

A knitted fabric that can be used for sensing tasks differs significantly from a fabric by its properties and by a completely different manufacturing method, because it forms stitches. A knitted fabric of this type is known from EP 1 997 952 A2, for example, and will be explained in more detail in the following with reference to FIGS. 1 and 2.

FIG. 1 shows a single-layer Intarsia knitted fabric 100' having electroconductive and non-electroconductive regions. Electroconductive yarns are knitted into the Intarsia knitted fabric 100' such that two intermeshing comb structures 101', 102' are formed. The two comb structures 101', 102' form two intermeshing electrodes, which are oriented in a first (horizontal) direction, for capacitive area monitoring. A first comb structure 101' is connected to a positive pole of a voltage supply device of an evaluation circuit and a second comb structure 102' is connected to a negative pole of the voltage supply device of the evaluation circuit. After connection to the voltage supply device, one of the two comb structures 101', 102' of the knitted fabric 100' is positively charged and the other of the two comb structures 101', 102' is negatively charged. An approach to the knitted fabric 100', for example, in which the two comb structures 101', 102' are formed, can thus be monitored capacitively. From a technical and functional perspective, the knitted fabric 100' acts like a plurality of open capacitors, each of which forms an electric field. Electric fields are thus formed between the two comb structures 101', 102' connected to the two poles of the electrical voltage supply device of the evaluation circuit. As soon as an object having a dielectric constant greater than the dielectric constant of air enters one of the electric fields, the capacitance of the electric field will change, and in particular will increase, depending on the material of the object. This change can be measured and evaluated using an appropriate evaluation unit of the evaluation circuit connected to the comb structures 101', 102'.

FIG. 2 shows an alternative form of a single-layer Intarsia knitted fabric 100", in which the electroconductive yarns are knitted such that the two intermeshing comb structures 101", 102" are oriented in a second (vertical) direction.

Using the comb structures 101', 102', 101", 102" of the knitted fabrics 100', 100" which are arranged as discussed above and respectively form a positively or a negatively charged electrode, it is only possible to monitor the entire area of the relevant Intarsia knitted fabric 100', 100" (without a corresponding spatial resolution), because all of the electrical conductors of each comb structure 101', 102', 101", 102" are electrically connected to one another.

SUMMARY

An improved shaped knitted fabric is provided, which can be produced in a simple and cost-effective manner and is in particular also suitable for sensory applications or switching applications having spatial resolution.

A shaped knitted fabric of the aforementioned type having the features of claim 1 is provided. The dependent claims describe further advantageous developments of the fabric and methods of using the fabric.

The shaped knitted fabric may comprise at least one first layer, into which a plurality of linear or flat, in particular strip-shaped, electroconductive structures made of an electroconductive yarn and linear or flat, in particular strip-shaped, non-electroconductive structures made of a non-electroconductive yarn are knitted such that the electroconductive structures are electrically insulated from one another, where each of the electroconductive structures can individually be electrically contacted and connected to an evaluation circuit. In comparison to the shaped knitted fabrics previously known from the state of the art, and due to the individual contactability of the electroconductive structures, the shaped knitted fabric can also be used, among other things, for sensor applications and switching applications having spatial resolution. Intarsia knitted fabrics are produced by switching a thread with a different thread of a different yarn at a specific position in a row of stitches instead of guiding the thread across the entire width of the shaped knitted fabric. Area sections of the shaped knitted fabric having different characteristics can thus be connected to one another in a simple manner. If all of the stitches of a shaped knitted fabric are knitted in the same size and on all of the participating needles, a rectangular flat knitted fabric area, for example, can be obtained.

Advantageously, the electroconductive structures and/or the non-electroconductive structures of the first layer are configured as Intarsia patterns or encircled areas.

Different knitting techniques, in particular variable stitch sizing, transferring stitches (for example using auxiliary needle beds), knitting, picking up stitches, splitting stitches and not knitting by selected needles, can for example be used to produce a knitted fabric area which corresponds to the progression of a surface of a shaped body. This results in a large variety of possible versions of the shaped knitted fabrics as described herein that cannot easily or not at all be obtained with technical fabrics having electroconductive and non-electroconductive structures.

According to one aspect, the shaped knitted fabric can provide an approach-sensitive, spatially resolving sensory area (surface), which can in particular be produced in a flat knitting process. Changes in the electric fields and/or other electric state variables when an object approaches can be detected by a suitable evaluation circuit connected to the electroconductive structures of the shaped knitted fabric.

Compared to a woven fabric comprising electroconductive and non-electroconductive structures, an at least one-layer shaped knitted fabric comprising the electroconductive and non-electroconductive structures produced as described herein may provide the following advantages:

improved stretch properties, whereby the stretch properties are brought about by the stitch structures of the shaped knitted fabric and not by the yarns used to produce the shaped knitted fabric, a significantly more flexible structure than that of a woven fabric, which tends to be comparatively stiffer, a different type of strain relief, significantly improved drapability, in particular also onto two-dimensional or three-dimensional surfaces having a complex shape, the possibility of creating a three-dimensional shape of the shaped knitted fabric right from the start during production.

In a particular form of a sensor arrangement, the single-layer shaped knitted fabric can be connected to an electrical voltage supply device of an evaluation circuit in a suitable manner, so that the individual electroconductive structures of the shaped knitted fabric can individually be electrically contacted. In other words, the single-layer shaped knitted fabric thus comprises partial electrode areas, which are formed by the electroconductive structures and can individually be electrically contacted. Due to the electrical voltage applied to them, these electroconductive structures can form electric fields relative to one another, so that an approach of objects and people, or rather body parts, can be detected with spatial resolution using the evaluation unit of the evaluation circuit. The changes in the electric fields between the electroconductive structures when an object approaches can thus be detected using the evaluation unit. The single-layer shaped knitted fabric can, for example, be used as a capacitive proximity sensor of a protective device for monitoring a technical installation.

Advantageously, in order to make electrical contact, the electroconductive structures are electrically connected in a punctiform manner with insulated microcables or insulated conductive yarns or wrapped yarns which are partially stripped at the contact point.

The insulated microcables or insulated conductive yarns or wrapped yarns can preferably be configured as filler threads which extend parallel to the stitch wales of the shaped knitted fabric. In doing so, the filler threads do not form stitches of the shaped knitted fabric.

In an advantageous further development, the shaped knitted fabric comprises at least one second layer connected to the first layer. The shaped knitted fabric can thus be provided with expanded functionalities or additional characteristics.

Advantageously, the second layer can be a knitted layer that is in particular connected to the first layer by knitting or is sewn to the first layer. A knitted connection of the layers, in particular, results in significant advantages with respect to production, because the first layer and the second layer of the shaped knitted fabric can be produced in a single knitting process, in particular in a flat knitting machine. The second layer can consist completely, or only partially, of a knitted fabric.

In another alternative, the second layer can, at least in sections, also include a woven fabric and/or a warp knitted fabric and/or a scrim and/or a nonwoven fabric and/or a foam material and/or a film. The second layer configured in this manner can be connected to the first layer during production by a textile connecting method, for example, by sewing, or also by material bonding, in particular by gluing.

Advantageously, the second layer can, for example at least in sections, be made of a non-electroconductive material. The second layer can advantageously be configured such that it provides protection against accidental contact for the first layer and/or electrical insulation for the electroconductive structures of the first layer.

The second layer can advantageously be made of an elastically deformable material. As a result of this measure, the second layer can additionally also form a mechanical shock absorbing or contact damping layer for the shaped knitted fabric.

According to an advantageous further development the shaped knitted fabric comprises a third layer, into which a plurality of linear or flat, in particular strip-shaped, electroconductive structures made of an electroconductive yarn, preferably as Intarsia patterns or encircled surfaces, and linear or flat, in particular strip-shaped, non-electroconductive structures made of a non-electroconductive yarn, preferably as Intarsia patterns or encircled surfaces, are knitted such that the electroconductive structures are electrically insulated from one another, wherein each of the electroconductive structures can individually be electrically contacted and connected to an evaluation circuit. This results in additional advantageous possible applications for the shaped knitted fabric in comparison to a single-layer or two-layer shaped knitted fabric.

The electrical circuitry/contact of the electroconductive structures of the first layer and the third layer with the evaluation circuit can be made possible or facilitated both by the incoming and outgoing electroconductive yarns and by the pattern-controlled incorporation of insulated microcables as filler threads or inlaid float threads. After the defined stripping of the microcables (for example by exposure to laser light), the punctiform contact of the electroconductive knitted yarns with insulated microcables or insulated conductive yarns can be achieved with conductive adhesives, soldering or oversewing with conductive sewing thread.

If the electroconductive structures of the first layer and the third layer are linear or flat, in particular strip-shaped, the linear or flat, in particular strip-shaped, electroconductive structures of the first layer can extend parallel to one another in a first direction and the linear or flat, in particular strip-shaped, electroconductive structures of the first layer can extend parallel to one another in a second direction, which is different from the first direction. The first direction and the second direction can in particular be two orthogonal spatial directions and constitute a horizontal and a vertical direction of the (flat) shaped knitted fabric. This advantageously creates a shaped knitted fabric having a crisscrossing, matrix-like structure of the electroconductive structures of the first layer and the electroconductive structures of the third layer so that, with the aid of a corresponding individual electrical contact of the evaluation circuit, a sensor arrangement having spatial resolution, for example, can be obtained. If the first direction and the second direction are not oriented orthogonally to one another, the matrix-like structure can also be oblique-angled or be a free-form surface.

Together with the evaluation circuit, the three-layer shaped knitted fabric according to this further development can thus form a sensor arrangement having at least one electrical property that changes as a result of an external force acting on the layers. Depending on the design of the second (middle) layer, the sensor arrangement can be configured as a capacitive sensor arrangement and/or as a piezoelectric sensor arrangement and/or as a resistive or piezoresistive sensor arrangement. Preferably not only the presence of a force acting on the shaped knitted fabric from the outside can be detected using the sensor arrangement, but also the magnitude of the force.

This three-layer shaped knitted fabric functions as a capacitive sensor arrangement when, from a technical functional perspective, the two outer electrodes, formed by the linear or flat, in particular strip-shaped, electrical structures of the first and third layer of the shaped knitted fabric, together with the intervening dielectric of the second layer, form a capacitor the capacitance of which changes as a result of the alteration of the spatial shape by a force. This change in the electric field can be detected by the evaluation unit of the evaluation circuit, which is connected to the electrodes of the first and third layer formed by the linear or flat, in particular strip-shaped electroconductive structures, and evaluated with spatial resolution.

The sensor arrangement with the three layers of the shaped knitted fabric functions resistively or piezoresistively if the external force causes the inner electrical resistance (volume resistance) between the two outer electrodes to change as a function of the external force when an electrical voltage is applied from the outside. This change in the volume resistance can be determined by a suitable evaluation unit of the evaluation circuit.

Such a sensor arrangement with the three layers of the shaped knitted fabric can conversely also be used as a piezoelectric sensor when electrical voltages, which can be measured with the aid of a suitable evaluation unit of the evaluation circuit, develop between the two outer electrodes of the outer layers as the result of an external force.

Depending on the configuration of the electronics, these different sensor principles discussed above can also be combined or used sequentially.

The connection of the second layer to the third layer of the shaped knitted fabric can preferably be accomplished using a textile connecting method, for example, in particular knitting or sewing, or also using a material bonding connecting method, in particular gluing.

In a particularly advantageous format, all three layers of the shaped knitted fabric are produced by knitting. This results in special manufacturing advantages, because all three layers of the shaped knitted fabric can be produced in a single knitting process, in particular in a flat knitting machine.

The second (middle) layer can in particular be knitted from a yarn having an existing, albeit low, electrical conductivity. The second layer can be made of a carbon-filled yarn, for example, which changes its electrical properties, such as its electrical volume resistance, as a function of the pressure. The yarn of which the second layer is knitted can, for example, alternatively also be made of a polymer filled with an electroconductive material (in particular carbon black or metal) or made of an intrinsically conductive polymer. This too changes its volume resistance as a function of the pressure.

Alternatively, the yarn of which the second layer is knitted can comprise a pressure-sensitive, electroconductive coating or can be made of a pressure-sensitive material.

If, as discussed above, the three-layer shaped knitted fabric is configured as a resistive sensor arrangement, the electroconductive structures of the first and the third layer can preferably be knitted as flat, in particular strip-shaped, structures, which are insulated from one another by narrow non-electroconductive regions or structures, which can likewise preferably be knitted in a linear or strip-shaped manner. The second (middle) layer is preferably knitted from a pressure-dependent electroconductive material. Knitting the three layers on top of one another thus creates a matrix structure that can provide pressure-dependent signals in a spatially resolved manner.

Another sensory variant is based on the second layer, which is connected to the first and the third layer of the shaped knitted fabric, being non-electroconductive. The electric field between the electroconductive structures of the two outer layers changes as a result of a compressive load or an approach. If the second layer is made of a non-electroconductive yarn, the result is a capacitive sensor arrangement. The second non-electroconductive layer forms a dielectric, so that the three-layer shaped knitted fabric forms a capacitive sensor arrangement in the manner of a plate capacitor.

Advantageously, openings can also be cut within the single or multilayer shaped knitted fabric, which in technical woven fabrics is possible only with great effort or not at all. The openings can alternatively also be produced by knitting.

In a particularly advantageous format, the width of the electroconductive structures of the first layer and/or the width of the electroconductive structures of the third layer can be greater than the width of the adjacent non-conductive structures of the respective layer. This measure advantageously minimizes the width of the non-electroconductive structures of the first layer and/or the third layer, so that the sensorically active surface portion of the shaped knitted fabric can correspondingly be maximized.

Therefore, with the aid of the shaped knitted fabric presented here, an approach-sensitive and/or pressure-sensitive, spatially resolving sensory area (surface) is created which, in particular in the flat knitting process, can be produced for different, even irregularly shaped, bodies without much manufacturing effort and which can, for example in a human-robot collaboration/interaction, be used to detect contacts between a human and a robot.

A further type of contact-sensitive sensor system is made possible if the second layer is not configured as a flat intermediate layer, but rather comprises a plurality of punctiform spacers to the first layer and/or to the third layer. After connection to a voltage supply device of the evaluation circuit, the electroconductive structures of the first layer and the non-electroconductive structures of the third layer have a different electrical potential. When pressure is applied, the mechanical resistance of the (in particular knitted) threads that form the spacers is overcome, so that the first layer and the third layer come into contact with one another. This creates an electrical signal that can be detected by the evaluation unit of the evaluation circuit, again with spatial resolution.

The shaped knitted fabric as described herein may be connected to an evaluation circuit for use as a sensor arrangement. As discussed above, such a shaped knitted fabric can be used as a sensor arrangement of a pressure-sensitive protective device for monitoring a technical installation.

The shaped knitted fabric may also be used as a switching device and/or as an input device. One possible application is a pressure-sensitive input device, for example, which can be used to carry out appropriate control inputs by pressing on relevant fields of the multilayer matrix-like shaped knitted fabric. A pressure-sensitive input keyboard can likewise be realized very easily using the multilayer matrix-like shaped knitted fabric.

A number of advantages of the shaped knitted fabric described herein can be summarized as follows:

- The drapability is considerably higher than in the case of woven fabrics.
- The stitch structure permits structural deformation not only within the area, but also when an object provided with the shaped knitted fabric is enclosed three-dimensionally.
- 2D and 3D shaping can be achieved during production by omitting stitches or by using variable stitch sizing. This is not possible when using a weaving technique.
- The Intarsia areas allow a free configuration of the area allocation for functional areas, independent of upper or lower layer of the shaped knitted fabric.
- Monomaterial Intarsia areas are possible, without the need to carry along another yarn material. This is not possible during weaving.
- Creating surface contact for electroconductive threads or the alternatively usable thin metallic wires/microcables is considerably easier when knitting than when weaving.
- A shaped knitted fabric is softer than a woven fabric.
- A shaped knitted fabric has better shock absorbing or contact damping properties than a woven fabric.
- Using the shaped knitted fabric as a sensory two-dimensional robot skin results in an additional reduction of injury risks (final emergency stop, absorption of the lag when the robot stops).

Examples of other areas of application of the fabric include:

- textile buttons or switches,
- tactile sensor applications,
- applications using gesture control,
- sensors and devices for human-robot/machine safety,
- seat occupancy detection and switching functions in vehicles (land vehicles, rail vehicles, aircraft or watercraft) or in furniture,
- position detection and location detection (for example of a person who has fallen), in particular on a carpet or on a carpeted floor,
- prevention of pinching and/or impact situations for machine components, buildings, furniture, doors, openings, etc.

BRIEF DESCRIPTION OF THE DRAWINGS

Further features and advantages will become apparent from the following description of preferred design examples with reference to the accompanying drawings. The figures show:

FIG. 1 is a single-layer Intarsia knitted fabric according to the state of the art having electroconductive and non-electroconductive structures, FIG. 2 is a further single-layer Intarsia knitted fabric having electroconductive and non-electroconductive structures according to the state of the art, FIG. 3 is a schematic diagram of a first design example of a single-layer shaped knitted fabric, FIG. 4 is a schematic diagram of a second design example of a single-layer shaped knitted fabric, FIG. 5 is a schematic diagram of a third design example of a single-layer shaped knitted fabric, FIG. 6 is a schematic diagram of a fourth design example of a single-layer shaped knitted fabric.

DETAILED DESCRIPTION

A first design example of a shaped knitted fabric 1a is explained in more detail below with reference to FIG. 3. In this case, the shaped knitted fabric 1a is configured as a circular knitted fabric which comprises a first layer 10 having electroconductive regions and non-electroconductive regions or structures 12. In this and in the other design examples, the electroconductive regions are produced from an electroconductive yarn. Electroconductive yarns can be made of a polymer filled with an electroconductive material, for example, in particular carbon black or metal, or consist of an intrinsically conductive polymer or be metallically conductive or coated with a conductive polymer or consist of fine metal wires or metal strands or include a core thread, around which fine metal wires or metal strands are wound.

Figure 11:
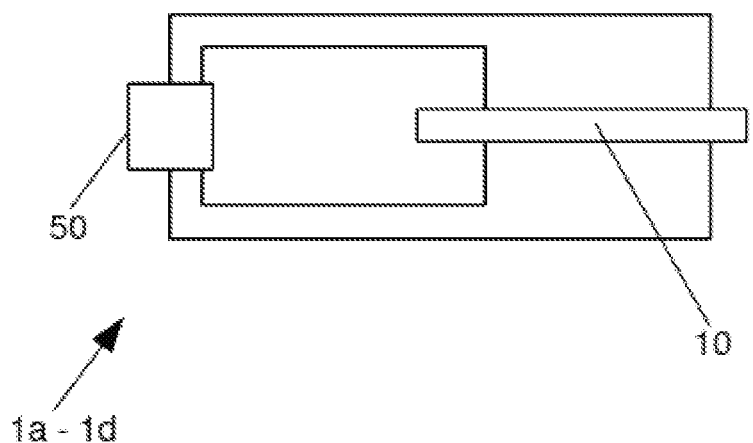
FIG. 11 is a schematic diagram illustrating an electrical connection of one of the shaped knitted fabrics of FIGS. 3 to 6 to an evaluation circuit.

The shaped knitted fabric 1a comprises a plurality of electroconductive structures 10a, 10b, 10c, 11a, 11b, 11c, which here extend in a first direction (in particular a horizontal direction) and are linear or alternatively flat, in particular strip-shaped, and are knitted from electroconductive yarns. The electroconductive structures 10a, 10b, 10c, 11a, 11b, 11c, which are oriented in the first direction and, in order to differentiate them more easily, are shown in FIG. 3 with continuous or broken lines (in reality they are of course not broken), form a continuous electroconductive line or strip arrangement in the first direction. Adjacent electroconductive structures 10a, 10b, 10c, 11a, 11b, 11c are electrically insulated from one another by the intervening non-electroconductive regions or structures 12. The linear or flat electroconductive structures 10a, 10b, 10c, 11a, 11b, 11c make it possible, for example, to use the shaped knitted fabric 1a in a sensor application for monitoring linear or strip-shaped regions in the first direction in which the electroconductive structures 10a, 10b, 10c, 11a, 11b, 11c extend. The electroconductive structures 10a, 10b, 10c, 11a, 11b, 11c are alternatingly in contact with a positive pole and a negative pole of an electrical voltage supply device (not explicitly shown here) of an evaluation circuit 50. The evaluation circuit 50 connected to the shaped knitted fabric 1a is shown in FIG. 11. This is one possible way, but not the only possible way, to connect the shaped knitted fabric 1a to the evaluation circuit 50. The electrical circuitry is in particular dependent on how the shaped knitted fabric 1a is being used.

The electroconductive structures 10a, 10b, 10c of the shaped knitted fabric 1a thus form a first group that is connected to the positive pole of the voltage supply device of the evaluation circuit 50. The electroconductive structures 11a, 11b, 11c, on the other hand, form a second group that is connected to the negative pole of the voltage supply device. The individual electrical contact of the electroconductive structures 10a, 10b, 10c of the first group with the positive pole of the voltage supply device of the evaluation circuit 50 and the electroconductive structures 11a, 11b, 11c of the second group with the negative pole of the voltage supply device of the evaluation circuit 50 can be achieved using a multicore electrical connecting cable, for example.

In the present case, the individual electrical contact (alternating between the positive pole and the negative pole) of the electroconductive structures 10a, 10b, 10c, 11a, 11b, 11c is in particular achieved via insulated microcables or insulated conductive yarns or wrapped yarns, which are configured as filler threads 20a, 20b, 20c, 21a, 21b, 21c that extend in a second direction (parallel to the stitch wales) and thus orthogonally to the first direction. The filler threads 20a, 20b, 20c, 21a, 21b, 21c are inlaid into the first layer 10 of the shaped knitted fabric 1a, without being formed into stitches. These filler threads 20a, 20b, 20c, 21a, 21b, 21c are partially stripped, for example with the aid of laser light, and respectively connected to one of the electroconductive structures 10a, 10b, 10c, 11a, 11b, 11c of the first layer 10 of the shaped knitted fabric 1a via an electroconductive connection 200a, 200b, 200c, 210a, 210b, 210c. Individual electrical contact for the electroconductive structures 10a, 10b, 10c, 11a, 11b, 11c is thus made possible. The electroconductive connections 200a, 200b, 200c, 210a, 210b, 210c can be achieved by sewing with an electroconductive sewing thread, for example, by gluing with an electroconductive adhesive or by crimping.

FIG. 4 shows a second design example of a shaped knitted fabric 1b designed as described herein. In this case, the shaped knitted fabric 1b is configured as an Intarsia knitted fabric which comprises a first layer 10 having electroconductive regions and non-electroconductive regions or structures 12. The shaped knitted fabric 1b comprises a plurality of electroconductive structures 10a, 10b, 10c, 11a, 11b, 11c which, at least in sections, here extend in a second direction (vertical direction) and are linear or alternatively flat, in particular strip-shaped, and are knitted from electroconductive yarns. The electroconductive structures 10a, 10b, 10c, 11a, 11b, 11c which, at least in sections, are oriented in the second (vertical) direction that extends orthogonally to the first direction according to FIG. 3 and are again shown in FIG. 4 with continuous or broken lines, respectively form a continuous line or strip arrangement. Adjacent electroconductive structures 10a, 10b, 10c, 11 a, 11b, 11c are thus electrically insulated from one another. The linear or flat electroconductive structures 10a, 10b, 10c, 11a, 11b, 11c make it possible to use the shaped knitted fabric 1a in a sensor application for monitoring linear or strip-shaped regions in the second (vertical) direction, for example, in which sections of the electroconductive structures 10a, 10b, 10c, 11a, 11b, 11c extend in this design example. The electroconductive structures 10a, 10b, 10c, 11a, 11b, 11c are alternatingly in contact with a positive pole and a negative pole of an electrical voltage supply device of the evaluation circuit 50. The electroconductive structures 10a, 10b, 10c thus form a first group that is connected to the positive pole of the electrical voltage supply device of the evaluation circuit 50. The electroconductive structures 11a, 11b, 11c, on the other hand, form a second group that is connected to the negative pole of the electrical voltage supply device of the evaluation circuit 50. The individual electrical contact (alternating between the positive pole and the negative pole) is hereby achieved directly via the electroconductive yarns knitted into the shaped knitted fabric 1b, from which the electroconductive structures 10a, 10b, 10c, 11a, 11b, 11c are formed.

A third design example of a single-layer shaped knitted fabric 1c is explained in more detail with reference to FIG. 5. The shaped knitted fabric 1c is configured as a knitted fabric having vertically inlaid filler threads and comprising a first layer 10 having electroconductive regions and non-electroconductive regions or structures 12. The shaped knitted fabric 1c comprises a plurality of electroconductive structures 10a, 10b, 10c, 11a, 11b, 11c which, at least in sections, here extend in a second (vertical) direction and are linear or alternatively flat, in particular strip-shaped, and consist of electroconductive yarns. The electroconductive structures 10a, 10b, 10c, 11a, 11b, 11c which, at least in sections, are oriented in the second (vertical) direction and are shown in FIG. 5 with continuous or broken lines, respectively form a continuous line or strip arrangement. Adjacent electroconductive structures 10a, 10b, 10c, 11a, 11b, 11c are thus electrically insulated from one another by the knitted non-electroconductive structures 12. The linear or flat electroconductive structures 10a, 10b, 10c, 11a, 11b, 11c make it possible, for example, to use the shaped knitted fabric 1a in a sensor application for monitoring linear or strip-shaped regions in the second (vertical) direction in which the electroconductive structures 10a, 10b, 10c, 11a, 11b, 11c extend. The electroconductive structures 10a, 10b, 10c, 11a, 11b, 11c are alternatingly individually in contact with a positive pole and a negative pole of an electrical voltage supply device of the evaluation circuit 50. The electroconductive structures 10a, 10b, 10c thus again form a first group, which is connected to the positive pole. The electroconductive structures 11a, 11b, 11c, on the other hand, form a second group that is connected to the negative pole.

As in the first design example, the individual electrical contact (alternating between the positive pole and the negative pole) of the electroconductive structures 10a, 10b, 10c, 11a, 11b, 11c is hereby achieved via insulated microcables or insulated electroconductive yarns or wrapped yarns, which are configured as filler threads 20a, 20b, 20c, 21a, 21b, 21c that extend in the second, in this case vertical, direction (parallel to the stitch wales). The filler threads 20a, 20b, 20c, 21a, 21b, 21c are again inlaid into the first layer 10 of the shaped knitted fabric 1a, without being formed into stitches. These filler threads 20a, 20b, 20c, 21a, 21b, 21c are partially stripped, for example with the aid of laser light, and respectively connected to one of the electroconductive structures 10a, 10b, 10c, 11a, 11b, 11c via an electroconductive connection 200a, 200b, 200c, 210a, 210b, 210c. They are thus in electrical contact. The electroconductive connections 200a, 200b, 200c, 210a, 210b, 210c can be achieved by sewing with a conductive sewing thread, for example, by gluing with an electroconductive adhesive or by crimping.

A single-layer shaped knitted fabric 1d designed as per a fourth design example of the present invention will be explained in more detail in the following with reference to FIG. 6. This represents a further development of the design example shown in FIG. 5. In terms of the arrangement of the electroconductive structures 10a, 10b, 10c, 11a, 11b, 11c in the first layer 10 and the electrical contact, the basic structure of the shaped knitted fabric 1d corresponds to that of the design example shown in FIG. 5. In this design example, the sections of the electroconductive structures 10a, 10b, 10c, 11a, 11b, 11c that extend in the second direction (vertical direction) are configured as Intarsia areas having a width of one or more stitches.

Each of the above-described single-layer shaped knitted fabrics 1a, 1b, 1c, 1d can in particular be used in sensor applications. To form a sensor arrangement, the single-layer shaped knitted fabric 1a, 1b, 1c, 1d can be connected to an electrical voltage supply device of the evaluation circuit 50 in a suitable manner, so that the individual electroconductive structures 10a, 10b, 10c, 11a, 11b, 11c of the shaped knitted fabric 1a, 1b, 1c, 1d can individually be electrically contacted. In other words, the single-layer shaped knitted fabric 1a, 1b, 1c, 1d comprises partial electrode areas which can be electrically contacted individually and, due to the electric voltages applied to them, form electric fields relative to one another. They are thus able to detect the approach of objects and people, or rather body parts.

In the event of an approach, the changes in the electric fields, for example, can be detected using a corresponding evaluation unit of the evaluation circuit 50 that is connected to the electroconductive structures 10a, 10b, 10c, 11a, 11b, 11c. Each of the above-described single-layer shaped knitted fabrics 1a, 1b, 1c, 1d can thus in particular be used as a capacitive proximity sensor of a protective device for monitoring a technical installation.

In further advantageous format, not explicitly shown here, which can expand the functionalities of the shaped knitted fabrics 1a, 1b, 1c, 1d, the above-described shaped knitted fabrics 1a, 1b, 1c, 1d can comprise at least one second layer connected to the first layer 10. The second layer can, for example, likewise be a knitted layer that is connected to the first layer 10 by knitting. This results in considerable manufacturing advantages, because the two layers of the shaped knitted fabric 1a, 1b, 1c, 1d can be produced in a single knitting process, in particular in a flat knitting machine. The second layer can alternatively also be sewn to the first layer 10. The second layer can consist completely, or alternatively also only partially, of a knitted fabric.

Alternatively, the second layer can also include a woven fabric and/or a warp knitted fabric and/or a scrim and/or a nonwoven fabric and/or a foam material and/or a film. The second layer constructed in this manner can be connected to the first layer by a textile connecting method, for example, in particular by sewing, or also by material bonding, in particular by gluing.

The second layer can be non-electroconductive, for example, and, from a technical functional perspective, provide protection against accidental contact for the first layer 10 and/or insulation for the electroconductive structures 10a, 10b, 10c, 11a, 11b, 11c of the first layer 10. If the second layer is made of an elastically deformable material, it can additionally also form a mechanical shock absorbing or contact damping layer for the shaped knitted fabric 1a, 1b, 1c, 1d.

Figure 7:
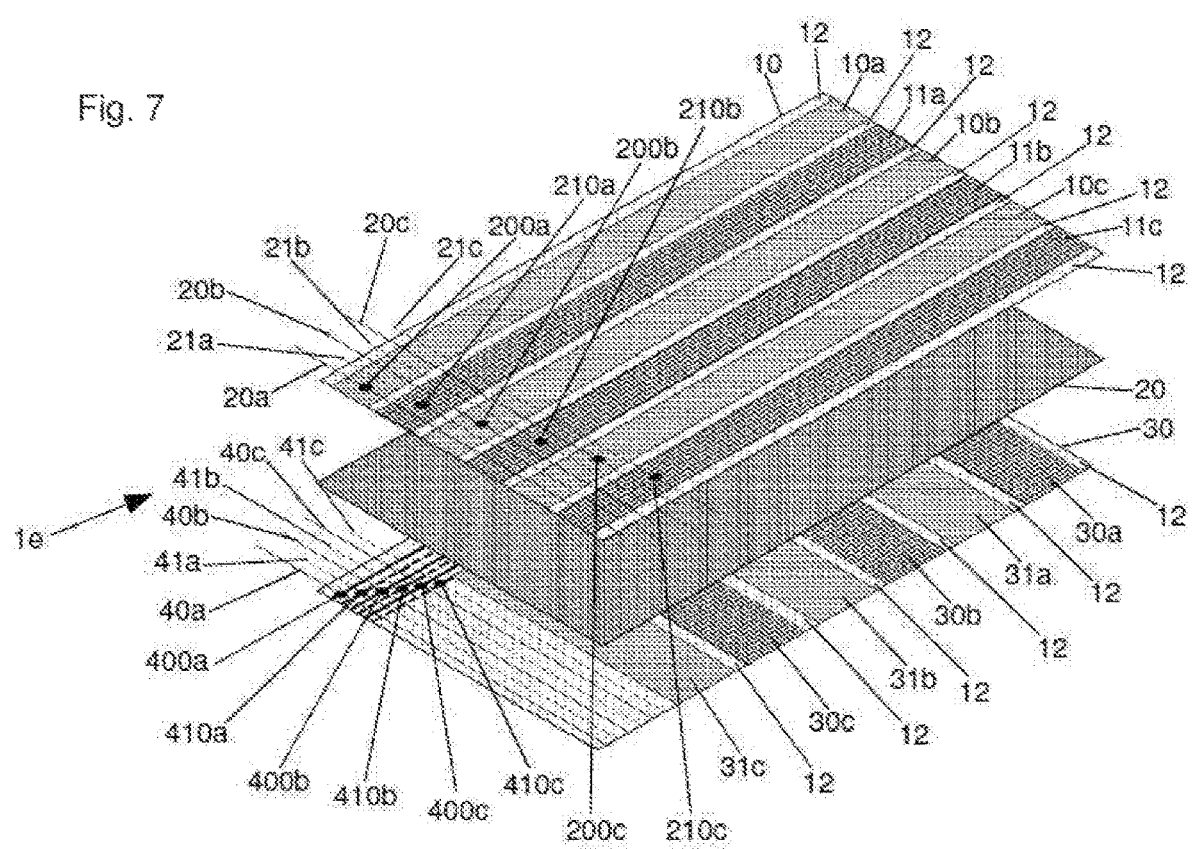
FIG. 7 is a perspective, exploded view of a fifth design example of a shaped knitted fabric.
Figure 8:
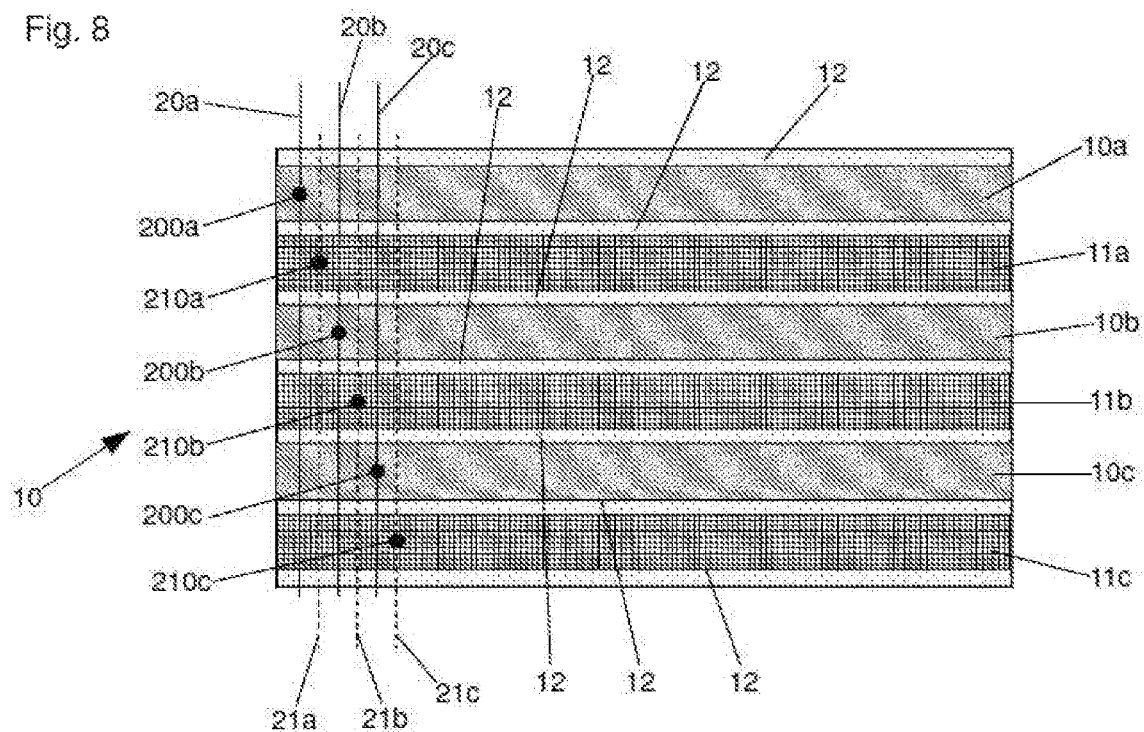
FIG. 8 is a schematic diagram of a possible construction of a first layer of the shaped knitted fabric of FIG. 7.
Figure 9:
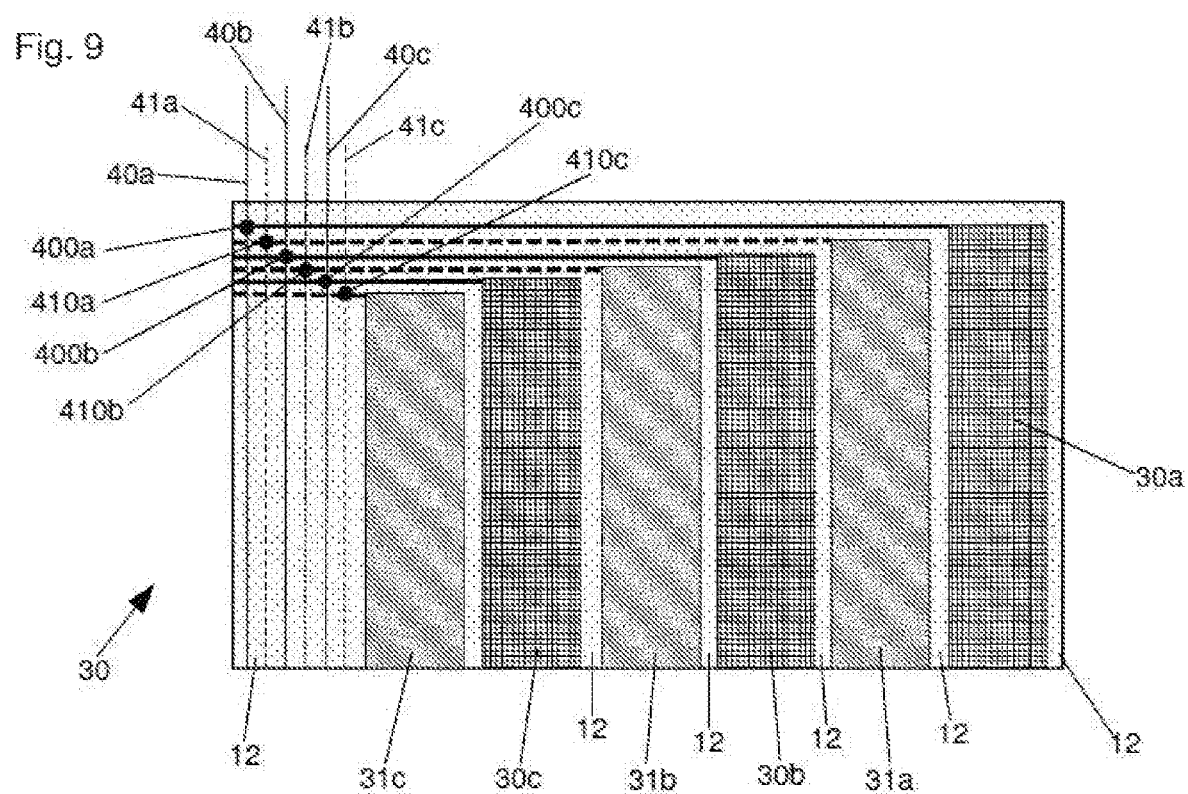
FIG. 9 is a schematic diagram of a possible construction of a third layer of the shaped knitted fabric of FIG. 7.
Figure 12:
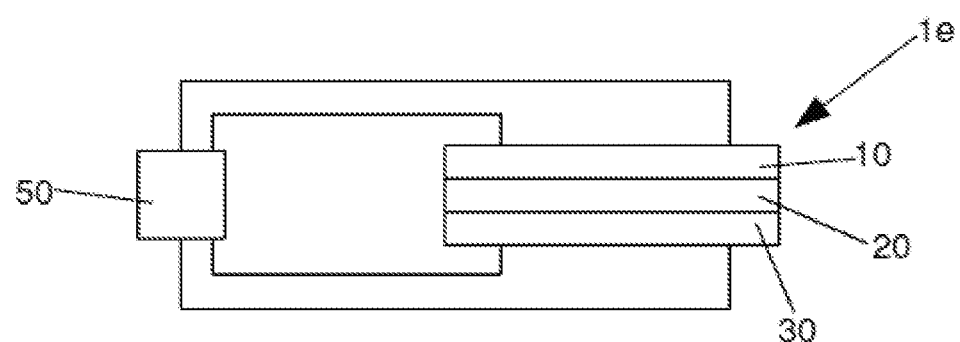
FIG. 12 is a schematic diagram illustrating an electrical connection of the shaped knitted fabric of FIG. 7 to an evaluation circuit.

A fifth design example of a shaped knitted fabric 1e will be explained in more detail in the following with reference to FIG. 7. The shaped knitted fabric 1e consists of three layers and comprises a first layer 10, a second layer 20 and a third layer 30, which are shown schematically in FIG. 7. FIG. 8 shows a possible structure for the first layer 10. A possible structure for the third layer 30 is shown in FIG. 9. FIG. 12 shows the shaped knitted fabric 1e after connection to the evaluation circuit 50. This is one possible way, but not the only possible way, to connect the shaped knitted fabric 1e to the evaluation circuit 50. The electrical circuitry is in particular dependent on how the shaped knitted fabric 1e is being used.

In this case, the first layer 10 of the shaped knitted fabric 1e is configured as a circular knitted fabric and comprises electroconductive regions and non-electroconductive regions or structures 12. The electroconductive regions are in turn made of an electroconductive yarn of the type already discussed above. The first layer 10 of the shaped knitted fabric 1e comprises a plurality of electroconductive structures 10a, 10b, 10c, 11a, 11b, 11c, which here extend in a first direction (horizontal direction) and are flat, in particular strip-shaped, and are knitted from electroconductive yarns. In this case, the electroconductive structures 10a, 10b, 10c, 11a, 11b, 11c are configured as encircled areas. The electroconductive structures 10a, 10b, 10c, 11a, 11b, 11c which are oriented in the first (horizontal) direction and are shown in FIG. 8 with continuous or broken lines, form a continuous strip arrangement in the first direction. Adjacent electroconductive structures 10a, 10b, 10c, 11a, 11b, 11c are thus electrically insulated from one another by the knitted non-electroconductive regions or structures 12. The electroconductive structures 10a, 10b, 10c, 11a, 11b, 11c which can individually be electrically contacted can, for example, alternatingly be in contact with a positive pole and a negative pole of an electrical voltage supply device of the evaluation circuit 50. The electroconductive structures 10a, 10b, 10c thus form a first group that is connected to the positive pole of the electrical voltage supply device. The electroconductive structures 11a, 11b, 11c, on the other hand, form a second group that is connected to the negative pole of the electrical voltage supply device.

The individual electrical contact (alternating between the positive pole and the negative pole) of the electroconductive structures 10a, 10b, 10c, 11a, 11b, 11c is hereby again achieved via insulated microcables or insulated conductive yarns or wrapped yarns, which are configured as filler threads 20a, 20b, 20c, 21a, 21b, 21c that extend in a second, in this case vertical, direction (parallel to the stitch wales). The filler threads 20a, 20b, 20c, 21a, 21b, 21c are inlaid into the first layer 10 of the shaped knitted fabric 1e, without being formed into stitches. These filler threads 20a, 20b, 20c, 21a, 21b, 21c are partially stripped, for example with the aid of laser light, and respectively connected to one of the electroconductive structures 10a, 10b, 10c, 11a, 11b, 11c via an electroconductive connection 200a, 200b, 200c, 210a, 210b, 210c. They are thus in electrical contact. The electroconductive connections 200a, 200b, 200c, 210a, 210b, 210c can be achieved by sewing with a conductive sewing thread, for example, by gluing with an electroconductive adhesive or by crimping.

A possible structure of a third layer 30 of the three-layer shaped knitted fabric 1e will be explained in more detail in the following with reference to FIG. 9. The third layer 30 is again configured as an Intarsia knitted fabric which comprises electroconductive regions and non-electroconductive regions 12. The third layer 30 comprises a plurality of electroconductive structures 30a, 30b, 30c, 31a, 31b, 31c which, at least in sections, here extend in a second direction (vertical direction) and in this design example are flat, in particular strip-shaped, and are knitted from electroconductive yarns. The electroconductive structures 30a, 30b, 30c, 31a, 31b, 31c are preferably configured as Intarsia areas having a width of one or more stitches.

The electroconductive structures 30a, 30b, 30c, 31a, 31b, 31c of the third layer 30 which, at least in sections, are oriented in the vertical direction and are shown in FIG. 9 with continuous or broken lines, respectively form a continuous strip arrangement. Adjacent electroconductive structures 30a, 30b, 30c, 31a, 31b, 31c are thus electrically insulated from one another by the knitted non-conductive regions 12. The electroconductive structures 30a, 30b, 30c, 31a, 31b, 31c which can individually be electrically contacted are alternatingly in contact with a positive pole and a negative pole of the electrical voltage supply device of the evaluation circuit 50. The electroconductive structures 30*a*, 30*b*, 30*c* thus form a first group, which is connected to the positive pole. The electroconductive structures 31*a*, 31*b*, 31*c*, on the other hand, form a second group that is connected to the negative pole.

As in the first design example, the electrical contact (alternating between the positive pole and the negative pole) of the electroconductive structures 30*a*, 30*b*, 30*c*, 31*a*, 31*b*, 31*c* of the third layer 30 is hereby achieved via insulated microcables or insulated conductive yarns or wrapped yarns, which are configured as filler threads 40*a*, 40*b*, 40*c*, 41*a*, 41*b*, 41*c* that extend in a second, in this case vertical, direction (parallel to the stitch wales). The filler threads 40*a*, 40*b*, 40*c*, 41*a*, 41*b*, 41*c* are inlaid into the third layer 30 of the shaped knitted fabric 1*e*, without being formed into stitches. These filler threads 40*a*, 40*b*, 40*c*, 41*a*, 41*b*, 41*c* are partially stripped, for example with the aid of laser light, and respectively connected to one of the electroconductive structures 30*a*, 30*b*, 30*c*, 31*a*, 31*b*, 31*c* via an electroconductive connection 400*a*, 400*b*, 400*c*, 410*a*, 410*b*, 410*c* and are thus in electrical contact. The electroconductive connections 400*a*, 400*b*, 400*c*, 410*a*, 410*b*, 410*c* can be achieved by sewing with a conductive sewing thread, for example, by gluing with an electroconductive adhesive or by crimping.

From the above explanations it becomes clear that the strip-shaped electroconductive structures 10*a*, 10*b*, 10*c*, 11*a*, 11*b*, 11*c* of the first layer 10 of the three-layer shaped knitted fabric 1*e* extend parallel to one another in a first direction, whereas the strip-shaped electroconductive structures 30*a*, 30*b*, 30*c*, 31*a*, 31*b*, 31*c* of the third layer 30 extend parallel to one another in a second direction different from the first direction. The first direction and the second direction are two orthogonal spatial directions and, in the present case, constitute a vertical and a horizontal direction of the shaped knitted fabric 1*e*. This creates a matrix-like structure of the electroconductive, individually contactable structures 10*a*, 10*b*, 10*c*, 11*a*, 11*b*, 11*c* of the first layer 10 and the electroconductive, individually contactable structures 30*a*, 30*b*, 30*c*, 31*a*, 31*b*, 31*c* of the third layer 30. Consequently, a sensor arrangement having spatial resolution in the first direction and in the second direction can be obtained. This matrix-like structure can alternatively also be oblique-angled or a free-form area.

The second layer 20 can be connected to the third layer 30 of the shaped knitted fabric 1*e* by a textile connecting method, for example, in particular by knitting or sewing, or also by material bonding, in particular by gluing. If all three layers 10, 20, 30 are produced by knitting, there are special advantages with respect to production, because all three layers 10, 20, 30 of the shaped knitted fabric 1*e* can be produced in a single knitting process, in particular in a flat knitting machine.

The second (middle) layer 20 of the shaped knitted fabric 1*e* can in particular be knitted from a yarn having an existing, albeit low, electrical conductivity. The second layer 20 can be made of a carbon-filled yarn, for example, which changes its electrical properties, such as its electrical volume resistance, as a function of the pressure. The yarn of which the second layer 20 is knitted can, for example, also be made of a polymer filled with an electroconductive material (in particular carbon black or metal) or made of an intrinsically conductive polymer. This too changes its volume resistance as a function of the pressure. In a further alternative, the yarn of which the second layer 20 is knitted can comprise a pressure-sensitive, electroconductive coating or can be made of a pressure-sensitive material.

The three-layer shaped knitted fabric 1*e* according to the third design example can thus be used in a sensor arrangement, which has at least one electrical property that changes as a result of an external force acting on the layers 10, 20, 30. Depending on the design of the second (middle) layer 20, the sensor arrangement can in particular be configured as a capacitive sensor arrangement and/or as a piezoelectric sensor arrangement and/or as a resistive or piezoresistive sensor arrangement. Preferably not only the presence of a force acting on the shaped knitted fabric 1*e* from the outside can be detected, but also the magnitude of this force (or the resulting pressure).

The multilayer shaped knitted fabric 1*e* functions as a capacitive sensor arrangement when the two outer electrodes, formed by the electroconductive structures 10*a*, 10*b*, 10*c*, 11*a*, 11*b*, 11*c* of the first layer 10 and the electroconductive structures 30*a*, 30*b*, 30*c*, 31*a*, 31*b*, 31*c* of the third layer 30, together with an intervening dielectric formed by the second layer 20, form a capacitor, the capacitance of which changes as a result of the alteration of the spatial shape by an external force. This change in the electric field can be detected by an evaluation unit of the evaluation circuit 50 connected to the shaped knitted fabric 1*e*, and evaluated with spatial resolution.

The sensor arrangement with the three-layer shaped knitted fabric 1*e* functions resistively or piezoresistively when the inner electrical resistance of the shaped knitted fabric 1*e* between the two outer electrodes, formed by the electroconductive structures 10*a*, 10*b*, 10*c*, 11*a*, 11*b*, 11*c* of the first layer 10 and the electroconductive structures 30*a*, 30*b*, 30*c*, 31*a*, 31*b*, 31*c* of the third layer 30, changes as a function of the external force.

The shaped knitted fabric 1*e* can conversely also be used as a piezoelectric sensor arrangement when electrical voltages between the two outer electrodes, formed by the electroconductive structures 10*a*, 10*b*, 10*c*, 11*a*, 11*b*, 11*c* of the first layer 10 and the electroconductive structures 30*a*, 30*b*, 30*c*, 31*a*, 31*b*, 31*c* of the third layer 30, develop as the result of an external force and can be measured with the aid of a suitable evaluation unit of the evaluation circuit 50.

Said different measurement methods can preferably also be combined or used sequentially.

If, as discussed above, the three-layer shaped knitted fabric 1*e* is configured as a resistive sensor arrangement, the electroconductive structures 10*a*, 10*b*, 10*c*, 11*a*, 11*b*, 11*c* of the first layer 10 and the electroconductive structures 30*a*, 30*b*, 30*c*, 31*a*, 31*b*, 31*c* of the third layer 30, can preferably be knitted as flat, in particular strip-shaped, structures, which are insulated from one another by narrow non-electroconductive structures 12, which can likewise preferably be knitted in a linear or strip-shaped manner. The second (middle) layer 20 is knitted from a pressure-dependent conductive material. Knitting the three layers 10, 20, 30 on top of one another thus creates a matrix structure that provides pressure-dependent signals in a spatially resolved manner.

Another sensory variant is based on the second layer 20, which is connected to the first layer 10 and the third layer 30, being non-electroconductive. The electric field between the electrical structures 10*a*, 10*b*, 10*c*, 11*a*, 11*b*, 11*c* of the first layer 10 and the electroconductive structures 30*a*, 30*b*, 30*c*, 31*a*, 31*b*, 31*c* of the third layer 30, which form the two outer layers of the shaped knitted fabric 1*e*, changes in response to a compressive load or an approach. If the second layer 20 is made of a non-electroconductive yarn, the result is a capacitive sensor arrangement. The second non-electroconductive layer 20 forms a dielectric, so that the three-layer shaped knitted fabric 1e forms a capacitive sensor arrangement in the manner of a plate capacitor.

The width of the electroconductive strip-shaped structures 10a, 10b, 10c, 11a, 11b, 11c of the first layer 10 and/or the width of the electroconductive strip-shaped structures 30a, 30b, 30c, 31a, 31b, 31c of the third layer 30 is preferably greater than the width of the adjacent non-conductive strip-shaped structures 12 of the respective layer 10, 30, which electrically insulates the electroconductive structures 10a, 10b, 10c, 11a, 11b, 11c, 30a, 30b, 30c, 31a, 31b, 31c in the two layers 10, 30 from one another. This measure advantageously minimizes the width of the non-electroconductive strip-shaped structures 12 of the first layer 10 and/or the third layer 30, so that the sensorically active area portion of the shaped knitted fabric 1e can correspondingly be maximized.

The three layers 10, 20, 30 of the shaped knitted fabric 1e can preferably be knitted one on top of the other in one knitting process such that the first layer 10 has the electroconductive, strip-shaped structures 10a, 10b, 10c, 11a, 11b, 11c in the first (horizontal) direction and the third layer 30 has the electroconductive strip-shaped structures 30a, 30b, 30c, 31a, 31b, 31c in the second (vertical) direction, and the second layer 20, which is electroconductive in dependence on the pressure, is arranged as an insulating layer between the other two layers. Electrically actuating the electroconductive structures 10a, 10b, 10c, 11a, 11b, 11c of the first layer 10 and the electroconductive structures 30a, 30b, 30c, 31a, 31b, 31c of the third layer 30 alternately over the course of time permits a spatially resolved detection of an approach and/or contact via the determination of horizontal and vertical coordinates. The spatial resolution, which can be obtained by using the sensorically active area structure, depends in particular on the knitted division of the area into conductive and non-conductive areas or regions. The overlaps of the areas in the two electrode planes, which form in the direction of the row of stitches starting with a single row of stitches or a float thread, or in the direction of the stitch wales with a single stitch wale or a filler thread, are critical in this case.

The three layers 10, 20, 30 can furthermore be connected to one another during production in a defined manner by knitting such that specific distances or contacts can be set, for example as a spacer knitted fabric. Special area shapes, which can be draped both 2-dimensionally and 3-dimensionally, can likewise be produced by knitting.

It is also possible to produce each one of the layers 10, 20, 30 of the three-layer shaped knitted fabric 1e individually first by knitting and then connect them to one another, in particular by sewing or gluing.

Figure 10:
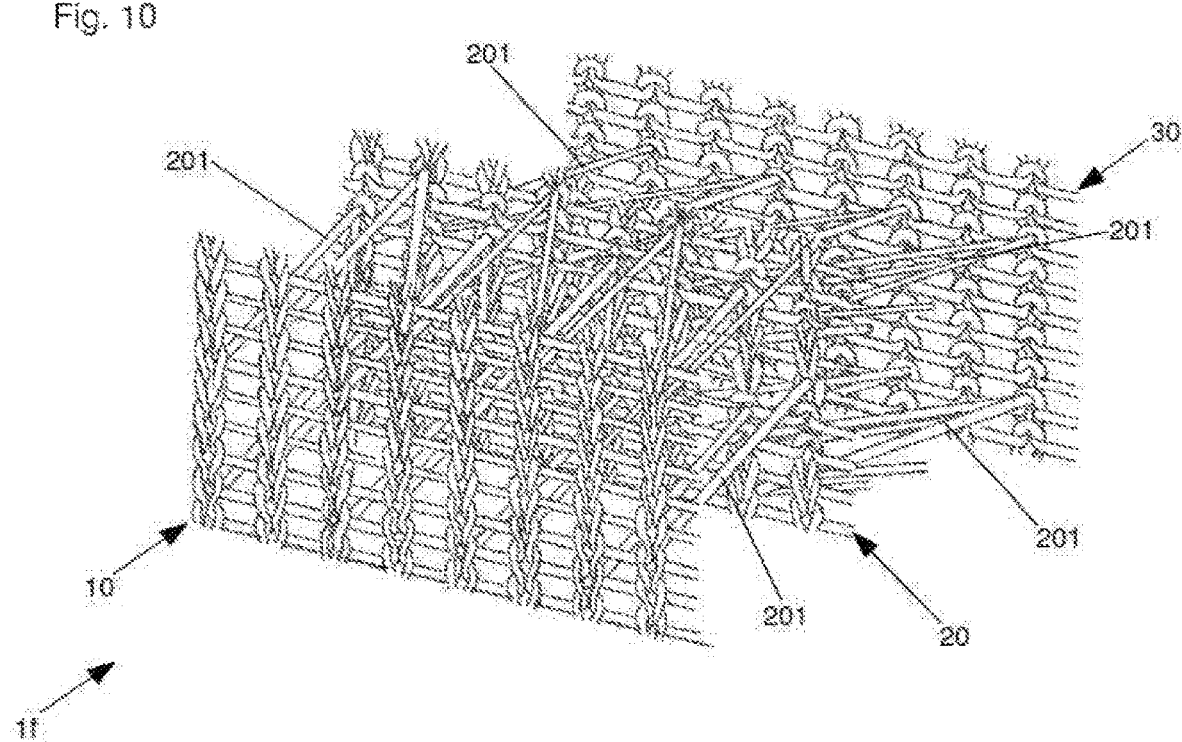
FIG. 10 is a perspective, exploded view of a sixth design example of a shaped knitted fabric.

A further type of contact-sensitive sensor system is made possible if the second layer 20 is not configured as a (flat) intermediate layer, but rather comprises a plurality of punctiform spacers 201 to the first layer 10 and to the third layer 30. Such a shaped knitted fabric 1f is shown in an exploded view in FIG. 10. After connection to a voltage supply device of the evaluation circuit 50, the electroconductive structures of the first layer 10 and the electroconductive structures of the third layer 30 have a different electrical potential. When pressure is applied, the mechanical resistance of the (in particular knitted) threads that form the spacers 201 is overcome, so that the first layer 10 and the third layer 30 come into contact with one another. This creates an electrical signal that can be detected by the evaluation unit of the evaluation circuit 50, again with spatial resolution.

The production of such a multilayer shaped knitted fabric 1f can in particular be carried out on a two-bed right-right flat knitting machine. The first layer 10 (on the front thread guide rails) is knitted using an Intarsia process on a front needle bed, for example. The second layer 20 is knitted on the even-numbered needles on a rear needle bed with a middle thread guide. And the third layer 30 is knitted as a circular structure on the odd-numbered needles on the rear needle bed with two thread guides for conductive and non-conductive yarn (for example on the two rearmost thread guide rails).

The mechanical connection of the three layers 10, 20, 30 amongst one another should preferably take place only in the regions that are not conductive on the electrode side. The connection can be made using tuck loops, for example, or by hooking stitches of the second (middle) layer into the non-conductive structures 12 of the first and third layer 10, 30, or by tuck loops or hooking stitches from the non-electroconductive structures 12 of the first and third layer 10, 30 into the second (middle) layer 20.

Further information about the production of the three-layer shaped knitted fabric 1f will be discussed in more detail in the following, again with reference to FIG. 10.

The first layer 10 is knitted on a front needle bed using every second needle, e.g., the odd-numbered needles. The third layer 30 is knitted on a rear needle bed, also using every second needle, e.g., the odd-numbered needles. The second (middle) layer 20 is knitted as needed on the remaining (even-numbered) needles on the front or the rear needle bed.

The three layers 10, 20, 30 are held together with a further thread, which is laid into the respective layers to be joined as tuck loops. Said thread is the thread in FIG. 10 with the straightened regions.

To produce the first and the second layer 10, 20, the second layer 20 is moved to the back. The first layer 10 is then knitted four times and the second layer 20 is knitted twice, each time with two connecting rows as tuck loops. The second layer 20 is then hung to the front and the second and third layer 20, 30 are formed accordingly. To do this, the third layer 30 is knitted four times and the second layer 20 is knitted twice, again with two connecting rows as tuck loops. After that, the process starts over from the beginning. The distance between the layers 10, 20, 30 of the shaped knitted fabric 1f can be adjusted via the relative offset of the needle beds with respect to one another and the type or length of the connecting threads and the frequency of incorporation.

What is claimed is:

1. A shaped knitted fabric comprising:
    at least one first layer, into which a first plurality of linear or flat electroconductive structures made of an electroconductive yarn and linear or flat non-electroconductive structures made of a non-electroconductive yarn are knitted such that the electroconductive structures are electrically insulated from one another, wherein
    each of the electroconductive structures is capable of being individually electrically contacted and connected to an evaluation circuit,
    in order to make electrical contact, the electroconductive structures are electrically connected in a punctiform manner with insulated microcables or insulated conductive yarns or wrapped yarns which are partially stripped at a contact point, and the insulated microcables or insulated conductive yarns or wrapped yarns are configured as filler threads which extend parallel to stitch wales of the shaped knitted fabric.

2. The shaped knitted fabric according to claim 1, wherein the electroconductive structures and/or the non-electroconductive structures of the first layer are configured as Intarsia patterns or encircled areas.

3. The shaped knitted fabric according to claim 1, wherein the shaped knitted fabric comprises at least one second layer which is connected to the first layer.

4. The shaped knitted fabric according to claim 3, wherein,
at least in sections, the second layer is a knitted layer which is in particular connected to the first layer by knitting or is sewn to the first layer.

5. The shaped knitted fabric according to claim 3, wherein, at least in sections, the second layer includes a woven fabric and/or a warp knitted fabric and/or a scrim and/or a nonwoven fabric and/or a foam material and/or a film.

6. The shaped knitted fabric according to claim 3 wherein, at least in sections, the second layer is made of a non-electroconductive material.

7. The shaped knitted fabric according to claim 3, wherein, at least in sections, the second layer is made of an elastically deformable material.

8. The shaped knitted fabric according to claim 3, wherein the shaped knitted fabric comprises a third layer, into which a second plurality of linear or flat electroconductive structures made of the electroconductive yarn and linear or flat non-electroconductive structures made of the non-electroconductive yarn, are knitted such that the electroconductive structures are electrically insulated from one another, wherein each of the electroconductive structures are capable of being individually electrically contacted and connected to an evaluation circuit.

9. The shaped knitted fabric according to claim 8, wherein the linear or flat electroconductive structures of the first layer extend parallel to one another in a first direction and that the linear or flat shaped, electroconductive structures of the third layer extend parallel to one another in a second direction, which is different from the first direction.

10. The shaped knitted fabric according to claim 9, wherein
said linear or flat electroconductive structures and/or said linear or flat non-electroconductive structures of said first layer and/or of said third layer are strip-shaped.

11. The shaped knitted fabric according to claim 8, wherein
the width of the electroconductive structures of the first layer and/or the width of the electroconductive structures of the third layer is greater than the width of the adjacent non-conductive structures of the respective layer.

12. The shaped knitted fabric according to claim 8, wherein the second layer includes a plurality of punctiform spacers to the first layer and/or to the third layer.

13. The shaped knitted fabric according to claim 8, wherein
said linear or flat electroconductive structures and/or said linear or flat non-electroconductive structures of said third layer are strip-shaped.

14. The shaped knitted fabric according to claim 8, wherein
said linear or flat electroconductive structures and/or said linear or flat non-electroconductive structures of said third layer are Intarsia patterns or encircled areas.

15. A shaped knitted fabric according to claim 1 wherein said linear or flat electroconductive structures and/or said linear or flat non-electroconductive structures are strip-shaped.

16. A sensor arrangement comprising a shaped knitted fabric according to claim 1 connected to an evaluation circuit.

17. A switching or input device comprising a shaped knitted fabric according to claim 1.

* * * * *